United States Patent [19]
Kobrin et al.

[11] Patent Number: 5,495,002
[45] Date of Patent: Feb. 27, 1996

[54] TUMOR ASSOCIATED MONOCLONAL ANTIBODY 123AV16

[75] Inventors: Barry J. Kobrin, Silver Spring; Martin V. Haspel, Seneca, both of Md.

[73] Assignee: Akzo N.V., Arnhem, Netherlands

[21] Appl. No.: 199,911

[22] Filed: Feb. 22, 1994

Related U.S. Application Data

[63] Continuation-in-part of Ser. No. 65,517, May 21, 1993, abandoned, which is a continuation of Ser. No. 636,179, Dec. 31, 1990, abandoned, which is a continuation-in-part of Ser. No. 302,155, Jan. 25, 1989, Pat. No. 5,106,738, which is a continuation-in-part of Ser. No. 697,078, Jan. 31, 1985, Pat. No. 4,828,991, which is a continuation-in-part of Ser. No. 575,533, Jan. 31, 1984, abandoned.

[51] Int. Cl.$^6$ .............................. C07K 16/30; C12N 5/22; C07H 15/12
[52] U.S. Cl. .................... 530/388.15; 530/387.3; 530/388.8; 530/388.1; 530/388.7; 536/23.53; 435/240.2; 435/240.27
[58] Field of Search .......................... 530/387.3, 387.7, 530/388.1, 388.15, 388.8; 435/240.2, 240.27, 172.2, 70.21; 536/23.53

[56] References Cited

U.S. PATENT DOCUMENTS

| | | |
|---|---|---|
| 4,172,124 | 10/1979 | Koprowski et al. |
| 4,196,265 | 4/1980 | Koprowski et al. |
| 4,340,586 | 7/1982 | Bekierkunst et al. |
| 4,471,057 | 9/1984 | Koprowski et al. |
| 4,522,918 | 6/1985 | Schlom. |
| 4,612,282 | 9/1986 | Schlom et al. |
| 4,613,576 | 9/1986 | Cote et al. |
| 4,618,577 | 10/1986 | Handley et al. |
| 4,661,586 | 4/1987 | Levy et al. |
| 4,828,991 | 5/1989 | Hanna et al. |
| 4,997,762 | 3/1991 | Hanna et al. |

FOREIGN PATENT DOCUMENTS

| | | |
|---|---|---|
| 0003173 | 1/1978 | European Pat. Off. |
| 9107492 | 5/1991 | WIPO. |
| 9311252 | 6/1993 | WIPO. |

OTHER PUBLICATIONS

Tsujimoto et al., Nucleic Acids Res. 12(22):8407–14, 1984
Morrison, Science 229:1202–1207, 1985.
Murray et al., Proc Am Assoc. Cancer Res. 33:340, 1992.
Jean L. Marx, "Monoclonal Antibodies in Cancer," *Science*, vol. 216 (1982), pp. 283–285.
Kohler and Milstein, *Nature*, vol. 256 (19), p. 495.
R. K. Oldman and R. V. Smalley, "Immunotherapy: The Old and the New," *J. Biol. Response Modifiers*, vol. 2 (1983), pp. 1–37.
Paul T. Stratte et al., "In Vivo Effects of Murine Monoclonal Anti–Human T Cell Antibodies in Subhuman Primates," *J. Biol. Response Modifiers*, vol. 1 (1982), pp. 137–148.
R. J. Cote et al., "Generation of Human Monoclonal Antibodies Reactive with Cellular Antigens," *Proc. Natl. Acad. Sci.*, vol. 80 (Apr. 1983), pp. 2026–2030.
H. C. Hoover, Jr. et al., "Delayed Cutaneous Hypersensitivity to Autologous Tumor Cells in Colorectal Cancer Patients Immunized with an Autologous Tumor Cell: Bacillus Calmette–Guérin Vaccine," *Cancer Research*, vol. 44 (Apr. 1984). pp. 1671–1676.
L. C. Peters et al., "Preparation of Immunotherapeutic Autologous Tumor Cell Vaccines from Solid Tumors," *Cancer Research*, vol. 39 (Apr. 1979), pp. 1353–1360.
L. Lindholm et al., "Monoclonal Antibodies against Gastrointestinal Tumour–Associated Antigens Isolated as Monosialogangliosides," *Int. Arch. Allergy Appl. Immuno.*, vol. 71 (1983), pp. 178–181.
H. Koprowski et al., *Somat. Cell Genet.*, vol. 5 (1979), pp. 957–972.
L. Ollson and H. S. Kaplan, "Human–human Hybridomas Producing Monoclonal Antibodies of Predefined Antigenic Specificity," *Proc. Natl. Acad. Sci.*, vol. 77, pp. 5429–5431.
J. L. Butler et al., "Delineation of Optical Conditions for Producing Mouse–Human Heterohybridomas from Human Peripheral Blood B Cells of Immunized Subjects," *J. Immunology*, vol. 130, No. 1, pp. 165–168.
Frederick Cancer Research Center Annual Report, 1980, "Immunotherapy," pp. 64–65.
R. Levy et al., *Annual Review of Medicine*, vol. 34, pp. 107–116 (1983).
M. Herlyn et al., *Proc. Natl. Acad. Sci., USA*, vol. 76(3), pp. 1438–1442 (Mar. 1979).
M. Herlyn et al., *J. Clinical Immunology*, vol. 2(2), pp. 135–140 (1982).
M. Herlyn et al., *Int. J. Cancer*, vol. 27, pp. 769–774 (1981).
Z. Steplewski et al., *Cancer Research*, vol. 41, pp. 2723–2727 (Jul., 1981).
*Stedman's Medical Dictionary*, 24th Ed., Williams & Wilkins, Baltimore, Md., (1982), p. 144.
*Handbook of Monoclonal Antibodies*, S. Ferrone et al., Eds. Noyes Pub. (1985), pp. 304–346.
*Monoclonal Antibodies in Clinical Medicine*, A. J. McMichael et al., Ed., Academic Press, London (1982), pp. 111–128, E. S. Lennox et al.
*Monoclonal Antibodies in Clinical Medicine*, A. J. McMichael et al., Ed., Academic Press, London (1982), pp. 17–35, Kaplan et al.
*Monoclonal Antibodies and Cancer*, B. D. Boss et al., Eds., Academic Press, Orlando (1983), pp. 135–142, N. N. H. Teng et al.
*Monoclonal Antibodies and Cancer*, B. D. Boss et al., Eds., Academic Press, Orlando (1983), pp. 143–155, K. A. Foon et al.
*Monoclonal Antibodies and Cancer*, B. D. Boss et al., Eds., Academic Press, Orlando (1983), pp. 163–170, M. C. Glassy et al.

(List continued on next page.)

Primary Examiner—Paula K. Hutzell
Attorney, Agent, or Firm—Mary E. Gormley

[57] ABSTRACT

This invention relates to transformed B-cell lines derived from peripheral blood B-cells of cancer patients actively immunized with autologous tumor antigen and the monoclonal antibodies they produce. These monoclonal antibodies can be used in both diagnostic procedures and therapy for human cancers.

2 Claims, 2 Drawing Sheets

OTHER PUBLICATIONS

*Monoclonal Antibodies and Cancer*, B. D. Boss et al., Eds., Academic Press, Orlando (1983), pp. 171–180, K. Sikora et al.

*Monoclonal Antibodies and Cancer*, B. D. Boss et al., Eds., Academic Press, Orlando (1983), pp. 181–184, P. A. W. Edwards et al.

D. Kozbor et al., *Proc. Natl. Acad. Sci.* vol. 79, pp. 6651–6655 (1982).

T. Takayama, *Nihon. Univ. J. Med.*, vol. 26, No. 5, Abstract, (1984).

J. E. Boyd et al., *Trends in Biotechnology*, vol. 2, No. 3, pp. 70–77, (1984).

D. L. Toffaletti et al., *J. of Immunology*, vol. 130, No. 6, pp. 2982–2986 (1983).

R. W. O'Donnell et al., *Som. Cell Mol. Gen.*, vol. 10, No. 2, pp. 195–204 (1984).

Haspel et al., *Cancer Research*, vol. 45, pp. 3951–3961 (Aug. 1985).

Finan et al., *Br. J. Cancer*, vol. 46, No. 1, Abstract (1982).

Sikora et al., *Br. J. Cancer*, vol. 43, No. 5, pp. 696–700.

Sikora et al., *Nature*, vol. 300, pp. 316–317.

Wunderlich et al., *Eur. J. Cancer Clin. Oncol.*, vol. 17, No. 7, pp. 719–730.

J. Schlom et al., *Prac. Natl. Acad. Sci., USA*, vol. 77, No. 11, pp. 6841–6845, (Nov. 1980).

Kohler, et al., *Nature*, vol. 256, pp. 495–498 (Aug. 1975).

Liao et al., *Cancer Research*, vol. 38, No. 12, pp. 4395–4400 (1978).

E. D. Sevier et al., "Monoclonal Antibodies in Clinical Immunology," *Clin. Chem.*, vol. 27, No. 11, pp. 1797–1806, 1981.

Kabat et al., *Sequences of Proteins of Immunological Interest* (5th Edition) US Dept. of Health and Human Serives, NIH Pub. No. 91–3242, pp. xvi–xvii.

L. C. Peters et al., "Preparation of Immunotherapeutic Autologous Tumor Cell Vaccines from Solid Tumors," Cancer Research, 39:1353–1360 (1979), US.

P. Chomczynski, "Single–Step Method of RNA Isolation by Acid Guanidium Thiocyananate–Phenol–Chloroform Extraction," Analytical Biochemistry, 162:156–159 (1987).

J. W. Larrick et al., "Polymerase Chain Reaction Using Mixed Primers: Cloning of Human Monoclonal Antibody Variable Region Genes from Single Hybridoma Cells," Bio/Technology, vol. 7, pp. 934–938, 1989.

J. G. Flanagan et al., "Mechanisms of Divergence and Convergence of the Human Immunoglobulin a1 and a2 Constant Region Gene Sequences," Cell, vol. 36:681–688 (1984).

123AV16-1 Light Chain

```
+1                                      +9   +11
Gln Ser Ala Leu Thr Gln Pro Pro Ser Val Ser Ala Ala Pro Gly
CAG TCT GCG TTG ACG CAG CCG CCC TCA GTA TCT GCG GCC CCA GGA

+17                          +24         27  27A 27B
Gln Lys Val Thr Ile Ser Cys Ser Gly Thr Ser Ser Asn Ile Gly
CAG AAG GTC ACC ATC TCC TGC TCT GGA ACC AGC TCC AAC ATT GGG
                                       |——————————CDR1 →
 30              34
Asn Asn Phe Val Ser Trp Tyr Gln Gln Phe Pro Gly Thr Ala Pro
AAT AAT TTT GTA TCC TGG TAC CAA CAA TTC CCA GGG ACA GCC CCC
————————————————|
 45              50                      56
Lys Leu Leu Ile Tyr Asp Asn Asn Lys Arg Pro Ser Gly Val Pro
AAA CTC CTC ATT TAT GAC AAT AAT AAG CGA CCC TCA GGG GTT CCT
                    |—————————CDR2——————————|
 60
Asp Arg Phe Ser Gly Ser Lys Ser Gly Thr Ser Ala Thr Leu Gly
GAC CGA TTC TCT GGC TCC AAG TCT GGC ACG TCA GCC ACC CTG GGC 75                                                      89
Ile Thr Gly Leu Gln Thr Gly Asp Glu Ala Asp Tyr Tyr Cys Gly
ATC ACC GGA CTC CAG ACT GGG GAC GAG GCC GAT TAT TAC TGC GGA
                                                         |——→
 90              95  95A 95B         97
Thr Trp Asp Thr Arg Leu Arg Ala Gly Val Phe Gly Gly Gly Thr
ACA TGG GAT ACC AGA CTG CGC GCT GGT GTG TTC GGC GGA GGG ACC
———CDR3——————————————————————————————————————————————|
                 107
Lys Leu Thr Val Leu
AAG CTG ACC GTC CTA
```

FIG. 1

123AV16-1 Heavy Chain

```
1
Glu Val Gln Leu Val Glu Ser Gly Gly Gly Leu Val Gln Pro Gly
GAG GTG CAA TTG GTG GAG TCT GGG GGA GGC TTG GTA CAG CCG GGG

16
Gly Ser Leu Arg Leu Ser Cys Glu Ala Ser Gly Phe Ser Arg Arg
GGG TCC CTG AGA CTC TCC TGT GAA GCC TCT GGA TTC AGC CGT CGG 31                  35a
Arg Ser Tyr Ala Ile Asn Trp Val Arg Gln Ala Pro Gly Lys Gly
CGG AGC TAT GCC ATA AAC TGG GTC CGC CAG GCT CCA GGG AAG GGG
        |————CDR1————|
45                 50      52a
Leu Glu Trp Val Ser Gly Met Ser Gly Ser Gly Ile Ser Thr Tyr
CTG GAG TGG GTC TCA GGT ATG AGT GGT AGT GGA ATC AGC ACA TAC
                        |————————————————CDR2——▶
59                  65
Tyr Ala Asp Ser Val Lys Gly Arg Phe Thr Ile Phe Arg Asp Ser
TAC GCA GAT TCC GTG AAG GGC CGG TTC ACC ATC TTC AGA GAC AGT 74                              82a 82b 82c
Ser Asn Asp Thr Leu Tyr Leu Asp Met Ile Asn Leu Arg Ala Glu
TCC AAT GAC ACG CTG TAT CTG GAC ATG ATC AAC CTG AGA GCG GAG 86                              95
Asp Thr Ala Thr Tyr Tyr Cys Ala Lys Thr Thr Thr Thr Val Thr
GAC ACG GCC ACA TAT TAC TGT GCG AAA ACG ACG ACT ACA GTG ACC
                                            |————————CDR3——▶
100a 100b 100c 100d 100e 101 102 103
Glu Phe Tyr Asp Met Asp Leu Trp Gly Gln Gly Thr Thr Val Thr
GAA TTC TAC GAT ATG GAC CTG TGG GGC CAA GGG ACC ACG GTC ACC
        |—————— 113          |
Val Ser Ser
GTC TCC TCA
```

TUMOR ASSOCIATED MONOCLONAL ANTIBODY 123AV16

This application is a continuation-in-part of U.S. patent application Ser. No. 08/065,517, now abandoned, filed May 21, 1993, which is a continuation of U.S. patent application Ser. No. 07/636,179, filed Dec. 31, 1990, now abandoned, which is a continuation-in-part of U.S. patent application Ser. No. 07/302,155, filed Jan. 25, 1989, now U.S. Pat. No. 5,106,738, which is a continuation-in-part of U.S. patent application Ser. No. 06/697,078, filed Jan. 31, 1985, issued as U.S. Pat. No. 4,828,991, which itself is a continuation-in-part of U.S. patent application Ser. No. 06/575,533, filed Jan. 31, 1984, now abandoned, all of which are included herein by reference.

DESCRIPTION OF THE INVENTION

This invention relates to a monoclonal antibody produced by a transformed B-cell line derived from B-cells of cancer patients actively immunized with autologous tumor antigen. This monoclonal antibody can be used in both diagnostic procedures and therapy for human cancers. Also part of this invention is the isolation and sequencing of the heavy chain and light chain variable regions and the identification of complementarity determining regions contained therein.

BACKGROUND OF THE INVENTION

This invention relates to new human monoclonal antibodies that react specifically with antigens associated with particular cancers and to the production of transformed B-cell lines derived from peripheral blood B-cells of actively immunized patients. This invention also relates to diagnostic procedures and cancer therapy using these monoclonal antibodies.

Currently available treatments for cancer, particularly radiation therapy and chemotherapy, are based upon the rationale that cancer cells are relatively more sensitive to these treatments than normal cells. However, severe toxicity for normal tissues imposes major limitations to these therapies. In contrast, antibody molecules exhibit exquisite specificity for their antigens. Researchers have therefore sought to isolate antibodies specific for cancer cells as the "long-sought 'magic bullet' for cancer therapy" (*Science*, 1982, 216:283).

Antibodies are protein molecules normally synthesized by the B-cell lymphocytes produced by bone marrow and carried in the blood stream. For any antigen entering the body, i.e., any foreign molecule from a simple organic chemical to a complex protein, antibodies are produced which recognize and attach to that particular chemical structure. The unique chemical structure on the antigen to which a particular antibody can bind is referred to as an antigenic determinant or epitope. B-cell lymphocytes in the body, referred to as B-cells, lymphocytes, or leukocytes, exist as hundreds of millions of different genetically programmed cells, each producing an antibody specific for a different determinant. An antigen, which stimulates antibody production, can have several determinants on its surface. On encountering an antigen, a B-cell carrying on its surface an antibody specific for a determinant on that antigen will replicate. This clonal expansion results in many daughter cells that secrete that antibody into the blood stream.

Because of the specificity of antibodies in recognizing and binding to antigens, it was desired to produce antibodies in quantity that are specific for a single determinant, thus binding only to antigens or tissues having that particular determinant.

B-cells do not grow in a continuous culture unless they have been altered by hybridization with an "immortal" cell or by being transformed with either viral or tumor DNA. Monoclonal antibodies are produced by B-lymphocyte cell lines that have been transformed, either spontaneously or intentionally, with a lymphotropic virus such as Epstein-Barr Virus (EBV). Transformation can also be accomplished using other transforming agents, such as viral DNA and cellular DNA. These cells, unlike hybridoma cells, possess a normal human diploid number (46) of chromosomes.

Monoclonal antibodies are synthesized in pure form uncontaminated by other immunoglobulins. With monoclonal antibody producing cells it is possible to produce virtually unlimited quantities of an antibody that is specific for one determinant on a particular antigen.

It has been believed that if antibodies specific for particular cancer cells were available, they could be used in various methods of treatment and diagnosis. Such antibodies could inactivate or kill particular tumor cells merely by attaching to the cell at the determinant for which they are specific. Alternatively, these antibodies may bind to the surface of effector lymphocytes or macrophages, converting them into tumor antigen-specific killer cells.

Monoclonal antibodies can also increase the specificity of chemotherapeutic drugs, toxins and radioactive isotopes, thus increasing their efficacy while decreasing their toxicity by being conjugated to them. In addition, antibodies conjugated with radionuclides or metallic tracers can be used for proton emission (PET) and nuclear magnetic resonance (NMR) imaging for in vivo diagnosis and localization of metastases. The antibodies can also be used for detecting the presence of tumor antigens in blood, as a diagnostic and/or prognostic test for cancer. Also, monoclonal antibodies can be used to isolate tumor antigens for potential use in a standardized vaccine.

In addition to the constant region, which is characteristic of the species, antibodies contain variable regions on both the heavy chain ($V_H$) and the light chain ($V_L$). These variable regions are the parts of the antibody that determine binding specificity and the variable region on every antibody that binds to a particular epitope is different from the variable regions on antibodies that bind to different epitopes. For the purpose of using antibody specificity to target drugs and radiometals for therapy and imaging, we believe that advantages can possibly be obtained by using only the portions of the antibodies active in binding for preparing immunoconjugates. Identifying and sequencing the complementarity determining regions of the heavy and light chains also provide information for synthesizing chimeric and multifunctional antibodies. For this reason, we isolated and sequenced the variable regions and determined the regions in the sequence that function to bind epitopes.

DESCRIPTION OF THE PRIOR ART

Past attempts at deriving monoclonal antibodies specific for human cancers have taken two routes with respect to B-cells: 1) B-cells have been extracted from spleens of mice that were immunized against human tumors, U.S. Pat. No. 4,172,124; and 2) human B-cells have been extracted from either peripheral blood or from lymph nodes draining tumors in cancer patients. Neither approach has yielded satisfactory results.

Mice immunized against human tumors have too broad a reactivity. That is, most of the mouse monoclonal antibodies generated react with human antigens present on normal as well as on tumor tissue. An antibody that reacts only with tumor cells is very difficult to select from among the large variety of antibodies produced. For example, 20,000 hybridomas derived from mice immunized with human small-cell lung carcinoma were screened for reactivity with tumor cells (*Science*, 1982, 216:283). In contrast to a very low frequency (<0.4%) observed by this research group, obtaining activated B-cells by the method used in the present invention results in up to 16% of the immortalized B-cells derived from immunized colon patients producing monoclonal antibodies that react specifically with tumor cells. In addition, monoclonal antibodies derived from mouse B-cells have limited potential for application in cancer therapy. After repeated administration they stimulate the human immune system to produce "anti-mouse" antibodies which, in clinical trials, have been shown to significantly diminish the efficacy of mouse monoclonal antibodies. The use of our human monoclonal antibodies can circumvent these difficulties. Use of the variable regions alone, or just the complementarity determining regions (CDR's), provides even less likelihood of immunogenicity as well as other advantages. The ability of smaller molecules, such as $V_H$ or even a single CDR, to rapidly clear from the body may be utilized in designing rapid in vivo diagnostic agents.

Another apparent difference between human and mouse monoclonal antibodies is their immunohistochemical staining pattern. Previous studies with mouse antibodies have demonstrated that there is often a heterogenous staining of cells within tumor sections. This pattern of reactivity has been attributed by some authors to antigenic heterogeneity of tumor cells (Hand et al., *Cancer Research*, 43:728–735, 1983). In contrast, the human monoclonal antibodies developed by our strategy were homogeneous in terms of their reactivity with tumors to which they did react. A plausible explanation for the heterogenous staining of mouse monoclonal antibodies is that it is a reflection of the murine immune recognition of phase- or cell-cycle-specific differentiation antigens abundant on the tumor cells rather than putative tumor associated antigens. It is not unreasonable to expect that when one immunizes mice with human tumor cells there would be substantial antigenic competition resulting in the more abundant and more predominant tissue-type and differentiation antigens successfully competing with relatively minor tumor associated antigens for immune responsiveness by the host. Thus, autologous immunization of man may result in the elicitation of antibodies against the group of antigens normally poorly immunogenic in mice. This evidence suggests that humans and mice may respond to different tumor antigens. In concert with this hypothesis is our finding that none of the first 36 human monoclonal antibodies we produced appeared to react with carcinoembryonic antigen (CEA), an antigen frequently recognized by murine monoclonal antibodies made against human tumor cells.

The majority of past attempts to develop human monoclonal antibodies have used B-cells extracted from either peripheral blood or lymph nodes from patients bearing tumors. It was believed that the presence of the antigenic tumor would cause a tumor-bearing individual to mount an immune response against his tumor and produce specifically immune B-cells. Thus, B-cells were taken from lymph nodes draining tumors in cancer patients or from circulating lymphocytes found in peripheral blood. However, prior to the present invention, there has been limited success in creating tumor-specific monoclonal antibodies.

The major problem in creating monoclonal antibodies specific for human tumor antigens has been the inability to find a source of specifically immune B-cells (*Science*, 1982, 216:285). In humans, the initial foci of cancer cells tend to grow over long periods of time, from 1% to 10% of the human lifespan, before there is any palpable clinical evidence of the disease. By this time patients are immunologically hyporesponsive to their tumors, or possibly immunologically tolerant. Thus, prior to the present invention, human monoclonal antibodies reactive with tumor cells could not reproducibly be obtained.

We have developed a new and more effective approach for obtaining monoclonal antibodies by using peripheral blood B-cells from patients immunized with cells from their own tumors in specific vaccine preparations. To achieve active specific immunotherapy, patients were immunized with autochthonous tumor cells, that is, cells from their own tumors. This approach was taken based on our theory that tumor cells express tumor-specific antigens.

Humans mounting an objective immune response against tumor cells were specifically found to be a good source of activated B-cells. We have shown that the peripheral blood of patients who had been actively immunized against their own tumors is an abundant source of such activated B-cells.

We demonstrated in clinical studies that an objective immune response is generated on treating patients having the particular cancer by skin testing, i.e., delayed cutaneous hypersensitivity (DCH). Immunized patients showed delayed cutaneous hypersensitivity to their own colorectal cancers. In addition, the monoclonal antibodies developed from the immunized patient's B-cells reacted with tumors of the same histological type in other patients. These results indicate that the patient's humoral immune response, production of antibodies, is directed against colorectal cancer generally and is not unique to the immunized patient's own tumor. This general response is especially important for the development of a standardized vaccine.

The generation of B-cells that produce antibodies having reactivity specific for epitopes on tumor cell associated antigens, particularly cell surface antigens as in the majority of cases, is an advantageous result that was speculative, at best, when the immunization studies were begun. Only the therapeutic effects of immunization were observed and measured during the animal studies on which the human immunization procedures were based, not the production of tumor specific antibodies.

The general immune response accompanied by an improvement in the subject's condition was indicative of a cellular response in which macrophages and T-cells become activated in the presence of tumor cell antigens and destroy the tumor cells. Although an antibody response would predictably be triggered by immunization under most circumstances, the time course of the antibody response and the cellular response would in most instances be different. Moreover, the fact that the patients were being immunized with autologous tumor cells, i.e., the patient's own tumor cells, and the experience of previous investigators that little or no antibody production is triggered by a patient's own tumor, made our discovery that B-cells that produce tumor specific antibodies are generated after immunization an unexpected beneficial result.

This invention is the result of our discovering ways to prepare successful vaccines for active specific immunization; developing procedures for extracting immunized human B-cells; and developing methods for sustained and continuous production of human monoclonal antibody producing cell lines and the production of monoclonal antibodies.

SUMMARY OF THE INVENTION

One object of the present invention was to develop human monoclonal antibodies specifically reactive with tumor-associated antigens and minimally reactive with antigens presented on non-tumor tissue. Such antibodies provide a means for detecting and diagnosing tumors and for treating patients with particular types of cancer. A further object was to identify a human monoclonal antibody that exhibits these properties, and to isolate, immortalize and culture the cell line producing this antibody. We also had as our objective sequencing the variable regions of the selected antibody, and isolating and identifying the portion of the heavy and light chains that actually bind to epitopes on these antigens, the complementarity determining regions (CDRs).

This invention comprises an EBV transformed human B-cell line, which produces human $IgA_1$ $\lambda_2$, namely the 123AV16 antibody, specifically reactive with an epitope found on a human colon tumor antigen, as well as identifying and sequencing the heavy and light chains and the complementarity determining regions of this antibody.

BRIEF DESCRIPTION OF THE FIGURES

FIG. 1 depicts the amino acid and nucleic acid sequences of the 12AV16-1 light chain variable region.

FIG. 2 depicts the amino acid and nucleic acid sequences of the 12AV16-1 heavy chain variable region.

DETAILED DESCRIPTION OF THE INVENTION

In the parent application Ser. No. 08/065,517 (abandoned), incorporated herein by reference, we disclosed an EBV transformed human B cell line, designated CO88BV59, which produces a human $IgG_3$ κ antibody specifically reactive with an epitope on a colon tumor antigen defined in application Ser. No. 07/929,842 filed Aug. 13, 1992 (U.S. Pat. No. 5,338,832).

We have now produced a human diploid cell line, an immortalized human B-cell line that we transformed by exposure to EBV, designated 123AV16, which produces a human IgA λ antibody that reacts with human colon tumor associated antigens. Our invention also includes cell lines derived therefrom (e.g., clones). For instance, by single cell cloning of the parent 123AV16 cell line, we have developed a clone: the cell line designated 123AV16-1. It also produces a human IgA λ antibody specifically reactive with the same antigen on human colon tumor cells. The antigen recognized by the IgA λ antibody is different from the antigen recognized by the 88BV59 and 16-88 antibodies (see, for instance, a comparison of Tables 2 and 3). Significantly, the IgA λ antibody reacts with a unique antigen and is more specific for human colon tumor cells than either the 16-88 or 88BV59 antibodies.

Disclosed herein are the complete sequences of the variable region of the heavy chain and the variable region of the light chain of the human monoclonal antibody derived from the cell line 123AV16-1. The sequence analysis indicates that the variable region is a member of the $V_H3$ family. The expressed $D_H$ segment was not homologous to known germline $D_H$ sequences and is not easily discernible. The expressed $J_H$ segment is $J_H6$. It is of note that there are three consecutive arginines at amino acids 29, 30 and 31 of the heavy chain variable region. The group of three consecutive arginines is a unique feature in these positions as compared to all known immunoglobulins in the Genbank and EMBL databases as of Jul. 30, 1993. The importance of having 3 arginines near or physically in a potential antigen binding site may be important in either contacting antigen or in maintaining a specific three-dimensional structure necessary for high avidity binding. With regard to the variable region of the light chain, the variable region family is the Vλ1. The expressed Jλ segment is Jλ2.

The locations and enumerations of the CDRs are shown in the Figures of the $V_H$ and $V_L$ sequences. For the $V_H$, CDR1 is at amino acids 31–35a. CDR2 encompasses amino acids 50–65. CDR3 encompasses amino acids 95–102. The entire $V_H$ is 113 amino acids. It will be noted that there are in fact a total of 123 amino acids within this sequence. This is because of the unique immunoglobulin enumeration nomenclature devised by Kabat et al. in Sequences of Proteins of Immunological Interest (5th Edition, United States Department of Health and Human Services, NIH Publication No. 91-3242). As outlined on the $V_H$ sequence, the enumeration includes amino acids at positions 35a, 52a, 82 a, b and c, and 100 a, b, c and d and e. These are the 10 additional amino acids that are marked by nomenclature within the $V_H$ on the basis of alignment with all other known immunoglobulin $V_H$ sequences.

Similarly, for the $V_L$, CDR1 encompasses amino acids 24–34. CDR2 encompasses amino acids 50–56. CDR3 encompasses amino acids 89–97. The complete $V_L$ is 107 amino acids according to the Kabat enumeration. In actuality, the number of amino acids in the $V_L$ is 110. Kabat's nomenclature revealed that there is no amino acid no. 10 within the sequence, and there are additional amino acids at positions 27a, 27b, 95a and 95b.

For purposes of this application we define a peptide comprising one or more of the CDRs to include any amino acid sequence that includes such CDRs, whether they are short sequences that would normally be called peptides, or long sequences that would normally be called proteins, or polypeptides in between.

EXAMPLE I

Preparation of Sensitized B-Cells

A. Patient Selection

Patients undergoing surgical resection of colon or rectal cancers were selected for a randomized trial of active specific immunotherapy. Randomization was done with stratification according to pathologic stage and tumor was obtained from all patients who met the clinical criteria. Candidates for the study were colorectal cancer patients with no previous history of cancer, who had received no prior chemotherapy or radiation therapy, and who were in suitable medical condition to comply with the outpatient treatment protocol. Patients eligible for the trial were those with tumor extending through the bowel wall (Astler-Coller B2), positive lymph nodes (stages C1, C2) or patients with metastatic disease (stage D). Within these classifications, patients were randomly selected for participation in treatment and non-treatment groups. Randomization cards were computer generated and sequentially drawn from each category postoperatively.

B. Tumor Acquisition

After surgical resection the bowel specimen was taken immediately to the hospital pathology department and opened under sterile conditions. Tumor tissue was excised, placed in sterile tubes containing Hank's Balanced Salt Solution (HBSS) containing 50 μg gentamicin per ml and carried immediately on ice to the laboratory for processing and freezing.

C. Dissociation of Solid Tumor and Colon Mucosa

The tissue dissociation procedure of Peters et al (*Cancer Research*, 39:1353–1360, 1979) was employed using sterile techniques throughout under a laminar flow hood. Tumor tissue was rinsed three times in the centrifuge tube with HBSS and gentamicin and transferred to a petri dish on ice. Scalpel dissection removed extraneous tissue and the tumor was minced into pieces approximately 2 to 3 mm in diameter. Tissue fragments were placed in a 75 ml flask with 20–40 ml of 0.14% (200 units/ml) Collagenase Type 1 (Sigma C-0130) and 0.1% (500 Kunitz units/ml) deoxyribonuclease type 1 (Sigma D-0876) (DNAase 1, Sigma D-0876) prewarmed to 37° C. Flasks were placed in a 37° C. waterbath with submersible magnetic stirrers at a speed which caused tumbling, but not foaming. After a 30-minute incubation free cells were decanted through three layers of sterile medium-wet nylon mesh (166t: Martin Supply Co., Baltimore, Md.) into a 50 ml centrifuge tube. The cells were centrifuged at 1200 rpm (250×g) in a refrigerated centrifuge for 10 minutes. The supernatant was poured off and the cells were resuspended in 5–10 ml of DNAase (0.1% in HBSS) and held at 37° C. for 5–10 minutes. The tube was filled with HBSS, washed by centrifugation, resuspended to 15 ml in HBSS and held on ice. The procedure was repeated until sufficient cells were obtained, usually three times for tumor cells. Cells from the different digests were then pooled, counted, and cell viability assessed by the trypan blue exclusion test. The cells were centrifuged for a final wash prior to cryopreservation.

D. Cryopreservation

Optimal cryopreservation was a primary concern. For vaccine preparation, the dissociated tumor cells were adjusted to $5-8\times10^7$/ml in HBSS and added in equal volume to chilled 2 X freezing medium containing 15% dimethylsulfoxide (DMSO) and 4% human serum albumin (HSA). The final suspension of 2 to $4\times10^7$ cells/ml were placed in 1.2 ml Nunc freezer vials. For DCH cell testing the procedure was the same except that no HSA was used. In both cases, in preparation for freezing, the Nunc vials were transferred on ice to a Cryo-Med model 990 Biological Freezer with a model 700 Controller and a model 500 Temperature Recorder for controlled-rate freezing. Care was taken that the temperature of the individual vials, including the monitor vial, was uniform at the beginning of the freezing process. Vials were cooled at a controlled rate of −1° C./min to a final temperature of −80° C. The vials were transferred in liquid nitrogen to liquid nitrogen storage.

E. Clinical Protocol

Patients with tumors of the appropriate pathologic stages were randomized to receive either the autologous tumor cell-BCG vaccine or to have no further therapy. The stage D patients all received 5-fluorouracil chemotherapy and all patients with lesions below the peritoneal reflection (rectal cancer) received 5040 rads of pelvic X-irradiation two weeks after immunotherapy was completed. The vaccines were started at 4–5 weeks after tumor resection to allow sufficient time for recovery of immunologic suppression induced by anesthesia and surgery. At 3–4 weeks after resection both control and treatment patients were skin tested with standard recall antigens as well as graded doses of their autologous tumor cells. Recall antigens used were: Mumps skin test antigen, USP, Eli Lilly, Indianapolis, Ind.; Aplisol, PPD, (Tuberculin Purified Protein Derivative), Parke-Davis, Detroit, Mich.; Trichophyton, diluted 1:30, Center Laboratories, Port Washington, N.Y.; and *Candida albicans* diluted 1:100, Center Laboratories, Port Washington, N.Y., 0.1 ml of each was placed intradermally on the forearm and examined for erythema and induration at 24 and 48 hours.

Patients selected for treatment protocol received 3 weekly intradermal vaccine injections consisting of $10^7$ irradiated, autologous tumor cells and $10^7$ BCG in the first 2 vaccines with $10^7$ tumor cells alone in the final. Fresh-frozen Tice BCG (Organon, Inc., West Orange, N.J., previously supplied by University of Illinois Medical Center, Chicago, Ill.) was stored at −70° C. The first vaccine was placed on the left anterior thigh approximately 10 cm below the groin crease, the second in a comparable location on the right thigh and the third in the right deltoid area.

F. Preparation of Vaccine

The criteria for successful vaccines are listed in Table 1. On the day of the first and second vaccinations, the vial was rapidly thawed in a 37° C. waterbath, tumor cells were diluted slowly to 15 ml in HBSS, washed once by centrifugation at 1200 rpm and resuspended to 15 ml in HBSS. Cell counts and viability determinations were made using the trypan blue exclusion test. Viability ranged between 70 and 90%, with a mean of 80%. The cells were washed once by centrifugation at 1200 rpm and resuspended to 15 ml in HBSS. The suspension of tumor cells was placed on ice and irradiated at 4020 rads/min for a total of 20,000 rads. The volume of the cell suspension was adjusted such that $10^7$ viable tumor cells remained in the tube ($1.3\times10^7$ viable cells are included to allow for cell loss in tubes and syringes, and for the possibility of approximately 20% misidentification of lymphoid cells). The cells were centrifuged, the supernatant removed and $10^7$ BCG were added in a volume of 0.1 ml. HBSS was added in sufficient quantity for a final volume of 0.2 ml. The third vaccine was similarly prepared, omitting the BCG.

The vaccine suspension was drawn up through a 20 gauge needle into a 1.0 ml tuberculin syringe. The 20 gauge needle was replaced with a 27 gauge needle for the intradermal injection, and the syringe was placed on ice for transport to the clinic.

The patients were observed closely after each vaccine for erythema and induration at the site of injections, fever, lymphadenopathy or any adverse reactions. The first two vaccine sites ulcerated after 2–3 weeks but always healed within 10 to 12 weeks.

EXAMPLE II

Production of Cells Producing Human Monoclonal Antibodies

A. Removal and Processing of Immunized B-Cells from Patients

Patients were bled at the time of the second immunization, one week after the first immunization, and at the time of the third vaccination, one week after the second immunization. Venous blood was collected aseptically in the presence of preservative-free heparin (O'Neill, Jones and Feldman, St. Louis, Mo.) at a final concentration of 17 units/mi. The blood was maintained at room temperature and transported to the laboratory expeditiously, within a few hours of collection.

The blood, diluted 1:2 with calcium and magnesium-free HBSS, was layered (4 ml) over 3 ml of lymphocyte separation medium (LSM, Litton Bionetics) and centrifuged in a 15 ml centrifuge tube for 30 minutes at 400×g. The cells at the interface were removed, diluted with three times their volume of HBSS and pelleted (1000 rpm for 10 minutes). The peripheral blood lymphocytes were resuspended in 10 ml of serum-free Hepes-buffered Dulbecco's MEM (DMEM), counted and viability determined.

B. EBV Transformation Procedure

Peripheral blood B-cells from immunized patients were intentionally exposed to transforming agents, resulting in continuously growing cell lines that produce monoclonal antibodies. We have used EBV as the transforming agent, although any effective lymphotropic virus or other transforming agent able to transform the B-cells to grow in continuous culture and still produce monoclonal antibodies specific for tumor associated antigens can be used.

By our method, heparinized blood was separated on an LSM gradient and the mononuclear cell fraction was collected at the interface. The mononuclear cell fraction can either be used at this point or cryopreserved for future transformation.

The lymphocytes, either fresh or cryopreserved, either unfractionated or depleted of some non-B cells, were counted and between 25 and $50 \times 10^6$ cells were pelleted. The pelleted cells were resuspended in 5 ml of freshly harvested Epstein Barr Virus in the form of undiluted B95-8 supernatant fluid harvested from a 4–6 day old culture of B95-8 cells, clarified by centrifugation at 2,000 rpm for 15 minutes at 4° C. and filtered through a 0.8 micron filter to insure that all cells had been removed. The B95-8 cell line was obtained from Dr. G. Tostado, Division of Biologics, FDA. The cells and EBV were incubated at 37° C. for 90 minutes for virus adsorption. During virus adsorption, the cells were agitated periodically. The cells were pelleted and then resuspended in BRI-2 (JRH Biosciences, Lenexa, Kans.) containing 10% FBS (BioWhittaker, Walkersville, Md.).

The cells were plated into wells containing irradiated feeder cells (such as J774). The mouse macrophage line J774 (ATCC, Rockville, Md.) had been irradiated (20,000 rads) and then cryopreserved. For this method feeder cells were thawed and then plated ($5 \times 10^2$ to $1 \times 10^3$ cells/well) into 96 well plates one day before the EBV transformation of the B-cell line.

The cell culture medium was changed twice per week for up to 6–8 weeks. Screening of supernatant fluid from wells exhibiting extensive cell growth to select those synthesizing human immunoglobulin and the culturing of selected cell lines was performed according to the procedures described in U.S. Pat. No. 4,828,911 for selection and culturing of monoclonal antibody producing cells.

Cells selected for producing human immunoglobulin were cultured and selected for tumor reactivity by screening against human tumor xenografts. 123AV16 was screened against a block consisting of four frozen sections of human colon carcinoma xenografts from nude mice. Xenograft sections and direct labeling of antibody were used in order to avoid the presence of human immunoglobulin.

C. Production of Monoclonal Antibodies

Human monoclonal antibody producing cells were grown in RPMI 1640 medium (Gibco, Grand Island, N.Y.) supplemented with 10% fetal bovine serum, 3 Mm L-glutamine and 5 µg/ml gentamicin. The medium was in some cases further supplemented with 25% D-glucose (final concentration 0.25%). The cells were at 37° C. (35°–38° C.) under a humidified atmosphere of 7.5% $CO_2$ in air. The antibody was harvested from the highly metabolized spent medium by pelletizing the medium free of cells (e.g., by centrifuging at 500 rpm for 15 minutes).

EXAMPLE III

Reactivity of Monoclonal Antibodies to Normal and Tumor Tissue

Most of the antibodies exhibited substantially reduced binding to normal colonic mucosa. The antibodies reactive with paraffin sections were also tested for reactivity with normal tissue. 123AV16 antibody showed negative reactivity with the following normal human tissues: ovary, prostate, kidney, breast, lung and pancreas. 123AV16 antibody exhibited slight reactivity with normal colon and stomach tissue. Table 2 shows the reactivity of 123AV16 with tumor tissue specimens.

In addition to providing monoclonal antibodies reactive with tumor associated antigens for the in vivo diagnosis and immunotherapy of cancer, the invention provides monoclonal antibodies that will be useful as probes to isolate and characterize the antigens relevant to human cancer immunity. These antigens may ultimately prove useful as a tumor vaccine. In addition, the generation of antibody producing diploid cells adds a dimension of genetic stability to the production of human monoclonal antibodies reactive with tumor associated antigens.

The foregoing describes the formation of novel monoclonal antibodies specific for certain tumors, monoclonal antibody producing cell lines, and methods for their preparation. It will be understood that many variations and modifications of the techniques disclosed herein are available to those of ordinary skill in the relevant art and that such variations and modifications are contemplated as being within the scope of the invention.

This invention is specifically directed to the cell line producing the IgA λ human monoclonal antibody 123AV16. The isotype of the human monoclonal antibody obtained from the cell line 123AV16-1 was determined by ELISA using 96 well polystyrene flat bottom immulon I microtitre plates (Dynatech, Alexandria, Va.) coated at 5 µg/ml with a goat anti-human IgG+IgA+IgM (KPL, Gaithersburg, Md.). Duplicate samples of the culture supernatants of purified IgG, IgA or IgM standards (OTC-Cappel, West Chester Pa.) diluted in BRI-2 containing 10% FBS were added to the wells and incubated at 37° C. for one hour. The plates were washed three times with PBS containing 0.5% TWEEN 20 (Sigma, St. Louis, Mo.) followed by the addition of specific HRP-conjugated antibodies to human γ, α or µ chains (KPL, Gaithersburg, Md.). The plates were incubated at 37° C. for one hour and then washed three times with PBS containing 0.5% TWEEN 20. Color development was achieved by the addition of TMB (100 µg/ml; Sigma, St. Louis, Mo.) in 0.1M sodium acetate buffer, pH 5.5, containing 0.003% hydrogen peroxide. The reaction was stopped by adding 50 µl 4N $H_2SO_4$ after 5–10 minutes at room temperature, and the absorbance was measured at 450 mM. The light chain isotype was determined by using an ouchterlony immunodiffusion kit (The Binding Site, San Diego, Calif.) following the manufacturer's instructions.

An IgA capture ELISA was used for quantitating the amount of human 123AV16-1 monoclonal antibody present in supernatants. A goat anti-human IgA (KPL, Gaithersburg, Md.) was used as the capture reagent with an HRP-labelled goat anti-human IgA conjugate (KPL, Gaithersburg, Md.) in the ELISA protocol described above. A purified human IgA (OTC-Cappel, West Chester, Pa.) was used as a standard.

EXAMPLE IV

Cloning and Sequencing 123AV16

Total RNA from 123AV16-1 (diploid) cells was prepared by the method of Chomczynski and Sacchi (*Analytical*

*Biochemistry*, Vol. 162:156–159, 1987). Briefly, cells were pelleted, imploded in 4 Molar guanidium isothiocyanate, 25 mM Sodium citrate pH 7.0, 0.5% Sarcosyl and 0.1M 2-Mercaptoethanol and RNA was extracted after the addition of 0.02M Sodium acetate pH 4.0, 1 volume of phenol and 0.2 volume chloroform. Samples were centrifuged 10,000 XG for 20 minutes at 4° C. and the aqueous phase transferred to a fresh tube and re-precipitated with one volume of isopropanol for one hour at −20° C. After a resuspension in the guanidium isothiocyanate-based solution and reprecipitation with isopropanol cell pellets were washed with 75% ethanol and resuspended in 0.5% SDS. Oligo dT cellulose chromatography (Aviv and Leder PNAS Volume 69:1408–1412, 1972) was performed to select for poly A (+) mRNA according to standard procedures.

cDNA Synthesis 1.2 μgs of 123AV16-1 poly A (+) was combined with 1 μg of Promega NotI oligo dT primer adapter by heating at 70° C. and chilling quickly on ice. (500 μM), of dNTPs and 200 units of Life Technologies Inc.'s Moloney Murine Leukemia Virus RNase H⁻ reverse transcriptase (Superscript)™ were added and incubated in 50 mM Tris HCl pH 8.3, 75 mM KCl, 3 mM $MgCl_2$ and 10 mM dTT for 30 minutes at 37° C. Second strand synthesis was performed via the addition of 187 μM dNTPs, 30 units *E. coli* DNA Polymerase I,15 units *E. coli* DNA Ligase and 1.4 units *E. coli* RNase H in 19 mM Tris HCl pH 6.9, 90 mM KCl, 4 mM $MgCl_2$, 125 μM β-Nad and 50 mM ammonium sulfate. After incubation at 16° C. for two hours the reaction was stopped with 50 mM EDTA and the cDNA was purified through phenol extraction and ethanol precipitation and resuspended in 11 μl of $dH_2O$. The polymerase chain reaction (Perkin-Elmer, Cetus PCR kit) was then performed with a 1 μl aliquot of the double stranded cDNA. Degenerate oligonucleotides which hybridize to $NH_2$-terminal leader sequences along with oligonucleotides complimentary to either the carboxyl terminus of light chain or to the 3' untranslated region of the mRNA of the heavy chain were utilized in the PCR reaction.

For the heavy chain, an equal molar mixture of 3 degenerate heavy chain oligonucleotides at a final concentration of 300 ng/ml were mixed according to the protocol of Larrick et al., *Biotechnology*, Volume 7, pages 934–938 (1989), incorporated herein by reference. The human heavy chain leader oligos, each represented a group as defined by Kabat et al., Sequences of Proteins of Immunological Interest, 1991, NIH Publication N 291-3242, and encode consensus sequences for each heavy chain group from amino acid −20 to −12 of the human heavy chain leader peptide.

As the human $IgA_1$ and $IgA_2$ sequences differ substantially at their carboxyl termini, the present inventors developed a strategy to obtain α-specific cDNA irrespective of the $A_1$ or $A_2$ isotype. We utilized sequences in the 3' untranslated region that were identical in both $IgA_1$ and $IgA_2$ (Flanagan et al., *Cell*, Volume 36, pages 682–686, 1984), to amplify α cDNA. To this end, an oligonucleotide complimentary to sequences 3' of the human IgA coding region within the α mRNA untranslated region was synthesized, purified and added to a final concentration of 300 ng/ml along with 1 X Cetus Taq polymerase buffer (500 mM KCl, 100 mM Tris-HCL, pH 8.3, 1.5 mM $MgCl_2$, 0.1% gelatin), 200 μM of each dNTP and 2.5 units of Cetus Taq polymerase in a final reaction volume of 50 μl.

For the light chain, the degenerate oligo, homologous to the human λ leader sequences as described by Larrick et al., *Biotechnology*, Volume 7, pages 934–938 (1989) was utilized along with an oligonucleotide complimentary to the carboxyl terminal amino acids 215-210 of the human λ constant region.

The PCR for the heavy chain was performed for 30 cycles with a 1 minute denaturation at 94° C., a 1 minute annealing at 55° C. and a 2 minute extension at 72° C. The light chain PCR was similar except the annealing step was for 1 minute at 47° C. PCRs were phenol extracted and after diluting up to 1.0 ml in 10 mM Tris pH 7.5, 1 mM EDTA, concentrated through a Centricon-100 membrane (Amicon Corp.), as per manufacturer's instructions. Diagnostic agarose gel electrophoresis was used to confirm the purity of each PCR reaction.

Sequencing of the heavy and light chain PCR products was performed using the BRL cycle sequencing kit (Life Technologies, Inc., Bethesda, Md.) according to manufacturer's specifications. Initially, the original 5' degenerate leader specific oligonucleotides were used to determine the $NH_2$ terminal 55 amino acids of the respective $V_H$ and $V_L$ regions.

Subsequently oligonucleotides were designed and synthesized from each sequence obtained. The sequence of the $V_H$ was completed using two oligonucleotides encoding amino acids 48–52a and amino acids 86–92 of the $V_H$. The sequence of the $V_L$ was completed using an oligonucleotide encoding amino acids 44–50 of $V_L$.

TABLE 1

CRITERIA FOR SUCCESSFUL VACCINES FOR ACTIVE SPECIFIC IMMUNOTHERAPY

Adjuvant (a) BCG (Phipps, Tice, Connaught); Lyophilized, frozen (dose-dependence > $10^6$ ($10^7$–$10^8$))
(b) C. parvum (Wellcome Labs) (dose-dependence > 7 μg (70 μg–700 μg))

Tumor Cells (a) Enzymatic dissociation
    (1) Collagenase type I (1.5–2.0 U/ml HBSS)
    (2) DNAase (450 D.U./ml HBSS)
    (3) 37° C. with stirring
(b) Cryopreservation
    (1) Controlled-rate freezing (−1° C./min) (7.5% DMSO, 5% HSA, HBSS)
    (2) Viability 80%
(c) X-irradiation
    (1) Rendered non-tumorigenic at 12,000–20,000 R.

Components and Administration[1]

(a) Ratio of adjuvant to tumor cells - 10:1 - 1:1 (optimum)
(b) $10^7$ tumor cells (optimum)
(c) 2–3 i.d. vaccinations at weekly intervals. Third vaccination contains tumor cells only.

[1]Isoniazid chemoprophylaxis of BCG infection optional.
BCG — Bacillus Calmette Guerin
HBSS — Hanks' Balanced saline solution
DMSO — Dimethylsulfoxide
HSA — Human serum albumin
R — Rads
PBS — Phosphate buffered saline
EDTA — Ethylenediaminetetraacetic acid

TABLE 2

TISSUE REACTIVITY OF 123AV16-1

| Tissue Type | Reactivity[a] to Tumor (%)[b] | Reactivity to Normal (%) |
| --- | --- | --- |
| Colon | | |
| Primary Tumor | 28/58 (48%) | 4/21 (19%) |
| Metastatic Tumor | 21/39 (54%) | — |
| | 7/19 (37%) | — |
| Kidney | 2/9 (22%) | 0/5 (0%) |
| Breast | 0/10 (0%) | 0/4 (0%) |

TABLE 2-continued

TISSUE REACTIVITY OF 123AV16-1

| Tissue Type | Reactivity[a] to Tumor (%)[b] | Reactivity to Normal (%) |
|---|---|---|
| Lung | 0/18 (0%) | 0/7 (0%) |
| Adenocarcinoma | 0/8 (0%) | — |
| Squamous | 0/1 (0%) | — |
| Small Cell | 0/8 (0%) | — |
| Melanoma | 0/8 (0%) | — |
| Ovary | 0/5 (0%) | 0/7 (0%) |
| Pancreas | 0/7 (0%) | 0/4 (0%) |
| Prostate | 0/10 (0%) | 0/2 (0%) |
| Stomach | 0/10 (0%) | 1/6 (16%) |

[a]Reactivity is defined as a staining intensigy of ≧ 2+ at a concentration of 2.5 µg/ml. Staining intensity is: 4+ strong; 3+ moderate; 2+ weak to moderate; 1+ weak.
[b]Number of reactive tissues/total number of specimens × 100.

TABLE 3

REACTIVITY OF 88BV59 WITH VARIOUS TUMOR TYPES

| Tumor Type | Number of Reactive Tissues | Total Number of Tissues Tested | Percentage |
|---|---|---|---|
| Colon | 74 | 84 | 88 |
| Breast | 22 | 23 | 99 |
| Ovarian | 16 | 20 | 80 |
| Pancreatic | 14 | 17 | 88 |
| Lung | | | |
| Adenocarcinoma | 6 | 6 | 100 |
| Squamous cell | 7 | 8 | 88 |
| Small cell | 0 | 1 | 0 |
| Prostate | 4 | 6 | 67 |
| Melanoma | 0 | 9 | 0 |

We claim:

1. An antibody that specifically binds a human colon tumor-associated antigen or antigens, comprising the $V_\lambda$ variable region amino acids 1 through 110 as depicted in SEQ ID NO: 2 linked to a human light chain constant region and the $V_H$ variable region amino acids 1 through 123 as depicted in SEQ ID NO:2 linked to a human heavy chain constant region.

2. The antibody of claim 1, wherein the $V_H$ variable region is linked to human IgA constant region.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 330 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: B-lymphocyte
        ( H ) CELL LINE: 123AV16

( v i i ) IMMEDIATE SOURCE:
        ( B ) CLONE: 123AV16-1

( i x ) FEATURE:
        ( A ) NAME/KEY: CDS
        ( B ) LOCATION: 1..330

( i x ) FEATURE:
    ( A ) NAME/KEY: misc_binding
    ( B ) LOCATION: 67..106

( i x ) FEATURE:
    ( A ) NAME/KEY: misc_binding
    ( B ) LOCATION: 152..173

( i x ) FEATURE:
    ( A ) NAME/KEY: misc_binding
    ( B ) LOCATION: 270..303

( x i ) SEQUENCE DESCRIPTION: SEQ ID NO:1:

```
CAG TCT GCG TTG ACG CAG CCG CCC TCA GTA TCT GCG GCC CCA GGA CAG     48
Gln Ser Ala Leu Thr Gln Pro Pro Ser Val Ser Ala Ala Pro Gly Gln
 1               5                  10                  15

AAG GTC ACC ATC TCC TGC TCT GGA ACC AGC TCC AAC ATT GGG AAT AAT     96
Lys Val Thr Ile Ser Cys Ser Gly Thr Ser Ser Asn Ile Gly Asn Asn
             20                  25                  30

TTT GTA TCC TGG TAC CAA CAA TTC CCA GGG ACA GCC CCC AAA CTC CTC    144
Phe Val Ser Trp Tyr Gln Gln Phe Pro Gly Thr Ala Pro Lys Leu Leu
         35                  40                  45

ATT TAT GAC AAT AAT AAG CGA CCC TCA GGG GTT CCT GAC CGA TTC TCT    192
Ile Tyr Asp Asn Asn Lys Arg Pro Ser Gly Val Pro Asp Arg Phe Ser
     50                  55                  60

GGC TCC AAG TCT GGC ACG TCA GCC ACC CTG GGC ATC ACC GGA CTC CAG    240
Gly Ser Lys Ser Gly Thr Ser Ala Thr Leu Gly Ile Thr Gly Leu Gln
 65                  70                  75                  80

ACT GGG GAC GAG GCC GAT TAT TAC TGC GGA ACA TGG GAT ACC AGA CTG    288
Thr Gly Asp Glu Ala Asp Tyr Tyr Cys Gly Thr Trp Asp Thr Arg Leu
                 85                  90                  95

CGC GCT GGT GTG TTC GGC GGA GGG ACC AAG CTG ACC GTC CTA            330
Arg Ala Gly Val Phe Gly Gly Gly Thr Lys Leu Thr Val Leu
                100                 105                 110
```

( 2 ) INFORMATION FOR SEQ ID NO:2:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gln Ser Ala Leu Thr Gln Pro Pro Ser Val Ser Ala Ala Pro Gly Gln
 1               5                  10                  15

Lys Val Thr Ile Ser Cys Ser Gly Thr Ser Ser Asn Ile Gly Asn Asn
             20                  25                  30

Phe Val Ser Trp Tyr Gln Gln Phe Pro Gly Thr Ala Pro Lys Leu Leu
         35                  40                  45

Ile Tyr Asp Asn Asn Lys Arg Pro Ser Gly Val Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Thr Arg Leu
                 85                  90                  95

Arg Ala Gly Val Phe Gly Gly Gly Thr Lys Leu Thr Val Leu
                100                 105                 110
```

( 2 ) INFORMATION FOR SEQ ID NO:3:

( i ) SEQUENCE CHARACTERISTICS:

(A) LENGTH: 369 base pairs
(B) TYPE: nucleic acid
(C) STRANDEDNESS: double
(D) TOPOLOGY: linear (i i) MOLECULE TYPE: cDNA (i i i) HYPOTHETICAL: NO (i v) ANTI-SENSE: NO (v i) ORIGINAL SOURCE:
(A) ORGANISM: Homo sapiens
(G) CELL TYPE: B-lymphocyte (v i i) IMMEDIATE SOURCE:
(B) CLONE: 123AV16-1

(i x) FEATURE:
(A) NAME/KEY: CDS
(B) LOCATION: 1..369

(i x) FEATURE:
(A) NAME/KEY: misc_binding
(B) LOCATION: 91..108

(i x) FEATURE:
(A) NAME/KEY: misc_binding
(B) LOCATION: 151..202

(i x) FEATURE:
(A) NAME/KEY: misc_binding
(B) LOCATION: 299..338

(x i) SEQUENCE DESCRIPTION: SEQ ID NO:3:

| GAG | GTG | CAA | TTG | GTG | GAG | TCT | GGG | GGA | GGC | TTG | GTA | CAG | CCG | GGG | GGG | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| TCC | CTG | AGA | CTC | TCC | TGT | GAA | GCC | TCT | GGA | TTC | AGC | CGT | CGG | CGG | AGC | 96 |
| Ser | Leu | Arg | Leu | Ser | Cys | Glu | Ala | Ser | Gly | Phe | Ser | Arg | Arg | Arg | Ser | |
| | | | 20 | | | | | 25 | | | | | 30 | | | |

| TAT | GCC | ATA | AAC | TGG | GTC | CGC | CAG | GCT | CCA | GGG | AAG | GGG | CTG | GAG | TGG | 144 |
| Tyr | Ala | Ile | Asn | Trp | Val | Arg | Gln | Ala | Pro | Gly | Lys | Gly | Leu | Glu | Trp | |
| | | 35 | | | | | 40 | | | | | 45 | | | | |

| GTC | TCA | GGT | ATG | AGT | GGT | AGT | GGA | ATC | AGC | ACA | TAC | TAC | GCA | GAT | TCC | 192 |
| Val | Ser | Gly | Met | Ser | Gly | Ser | Gly | Ile | Ser | Thr | Tyr | Tyr | Ala | Asp | Ser | |
| | 50 | | | | | 55 | | | | | 60 | | | | | |

| GTG | AAG | GGC | CGG | TTC | ACC | ATC | TTC | AGA | GAC | AGT | TCC | AAT | GAC | ACG | CTG | 240 |
| Val | Lys | Gly | Arg | Phe | Thr | Ile | Phe | Arg | Asp | Ser | Ser | Asn | Asp | Thr | Leu | |
| 65 | | | | | 70 | | | | | 75 | | | | | 80 | |

| TAT | CTG | GAC | ATG | ATC | AAC | CTG | AGA | GCG | GAG | GAC | ACG | GCC | ACA | TAT | TAC | 288 |
| Tyr | Leu | Asp | Met | Ile | Asn | Leu | Arg | Ala | Glu | Asp | Thr | Ala | Thr | Tyr | Tyr | |
| | | | | 85 | | | | | 90 | | | | | 95 | | |

| TGT | GCG | AAA | ACG | ACG | ACT | ACA | GTG | ACC | GAA | TTC | TAC | GAT | ATG | GAC | CTG | 336 |
| Cys | Ala | Lys | Thr | Thr | Thr | Thr | Val | Thr | Glu | Phe | Tyr | Asp | Met | Asp | Leu | |
| | | | 100 | | | | | 105 | | | | | 110 | | | |

| TGG | GGC | CAA | GGG | ACC | ACG | GTC | ACC | GTC | TCC | TCA | | | | | | 369 |
| Trp | Gly | Gln | Gly | Thr | Thr | Val | Thr | Val | Ser | Ser | | | | | | |
| | | 115 | | | | | 120 | | | | | | | | | |

(2) INFORMATION FOR SEQ ID NO:4:

(i) SEQUENCE CHARACTERISTICS:
(A) LENGTH: 123 amino acids
(B) TYPE: amino acid
(D) TOPOLOGY: linear (i i) MOLECULE TYPE: protein (x i) SEQUENCE DESCRIPTION: SEQ ID NO:4:

```
Glu  Val  Gln  Leu  Val  Glu  Ser  Gly  Gly  Gly  Leu  Val  Gln  Pro  Gly  Gly
 1              5                        10                  15

Ser  Leu  Arg  Leu  Ser  Cys  Glu  Ala  Ser  Gly  Phe  Ser  Arg  Arg  Arg  Ser
              20                       25                       30

Tyr  Ala  Ile  Asn  Trp  Val  Arg  Gln  Ala  Pro  Gly  Lys  Gly  Leu  Glu  Trp
         35                       40                      45

Val  Ser  Gly  Met  Ser  Gly  Ser  Gly  Ile  Ser  Thr  Tyr  Tyr  Ala  Asp  Ser
     50                       55                  60

Val  Lys  Gly  Arg  Phe  Thr  Ile  Phe  Arg  Asp  Ser  Ser  Asn  Asp  Thr  Leu
 65                      70                   75                              80

Tyr  Leu  Asp  Met  Ile  Asn  Leu  Arg  Ala  Glu  Asp  Thr  Ala  Thr  Tyr  Tyr
                   85                       90                            95

Cys  Ala  Lys  Thr  Thr  Thr  Thr  Val  Thr  Glu  Phe  Tyr  Asp  Met  Asp  Leu
              100                      105                      110

Trp  Gly  Gln  Gly  Thr  Thr  Val  Thr  Val  Ser  Ser
          115                 120
```